(12) United States Patent
Kim

(10) Patent No.: US 6,482,152 B2
(45) Date of Patent: Nov. 19, 2002

(54) SURGICAL TUNNEL RETRACTOR

(76) Inventor: Daniel S. Y. Kim, 215 Dubois Ct., Vancouver, WA (US) 98661

( * ) Notice: Subject to any disclaimer, the term of this patent is extended or adjusted under 35 U.S.C. 154(b) by 0 days.

(21) Appl. No.: 09/834,444

(22) Filed: Apr. 12, 2001

(65) Prior Publication Data

US 2002/0151769 A1 Oct. 17, 2002

(51) Int. Cl.$^7$ .................................................. A61B 1/32
(52) U.S. Cl. ........................ 600/210; 600/201; 606/83; 433/80
(58) Field of Search .............................. 606/83, 86, 87, 606/79; 433/72, 75, 140, 141, 215, 80; 600/235, 210, 204, 201, 206, 218, 226

(56) References Cited

U.S. PATENT DOCUMENTS

| | | | |
|---|---|---|---|
| 3,288,131 A | * 11/1966 | Garland ...................... 600/210 |
| 4,024,639 A |   5/1977 | Weiss et al. |
| 4,694,826 A | *  9/1987 | Chester ...................... 600/210 |
| 4,872,840 A |  10/1989 | Bori |
| 4,976,717 A | * 12/1990 | Boyle ......................... 606/119 |
| 5,397,235 A |   3/1995 | Elia |
| 5,759,033 A |   6/1998 | Elia |
| 5,885,291 A | *  3/1999 | Moskowitz et al. .......... 606/79 |
| 5,891,147 A |   4/1999 | Moskovitz et al. |
| 5,915,962 A |   6/1999 | Rosenlicht |
| 5,961,329 A |  10/1999 | Stuck-McCormick |
| 6,083,225 A |   7/2000 | Winslow et al. |
| 6,086,592 A | *  7/2000 | Rosemberg et al. .......... 606/86 |
| 6,241,519 B1 | *  6/2001 | Sedelmayer ................. 433/72 |
| 6,312,377 B1 | * 11/2001 | Segermark et al. .......... 600/210 |

* cited by examiner

*Primary Examiner*—Pedro Philogene
(74) *Attorney, Agent, or Firm*—Kurt M. Rylander

(57) ABSTRACT

An instrument for broaching and dilating an incision of soft tissue in a tunnel-like shape, the instrument stretches and supports tissue to allow the insertion and passage materials, and comprises a handle, and one or more arched plate members.

9 Claims, 1 Drawing Sheet

SURGICAL TUNNEL RETRACTOR

FIELD OF THE INVENTION

The present invention relates to an instrument for use by dentists or surgeons for retracting and opening incisions in soft tissue, and more particularly to dental instruments used in the operation of bone grafting augmentation.

BACKGROUND

It is common in dentistry to build up the gum tissue of individuals who have lost their teeth and suffered bone decay in the alveolar process to provide support for artificial teeth. In cases in which there are natural abutment teeth of sufficient strength and rigidity, artificial teeth may be supported by conventional bridgework. However, this is not always the case, and it then becomes necessary to either implant a support structure in the jaw bone, or to build up the alveolar ridge of the jaw bones to provide a firm base on which to mount the artificial tooth.

Often surgical and dental procedures require the insertion of substitute bone graft materials or implant material through narrow and small incisions in tissue and it is desirably done with the incision retracted open to sufficient aperture to allow unhindered passage of materials of various shape and length with minimal trauma to receiving tissue. In dental procedures for augmentation of the alveolar ridge graft material, such as strings of hydroxyapatite pearls, is inserted in the narrow tunnel-like space between the gingival soft connective tissue and the alveolar ridge of the mandible.

Known methods of building up the alveolar ridge of jawbones include cutting a long incision along the gum tissue, inserting the graft material along the alveolar ridge, and stitching the gum over the graft material or, alternatively, cutting a small incision, spreading the incision, and inserting a tubule of graft material into the incision and along under the gum tissue and along the alveolar ridge, and then stitching up the incised gum opening. Cutting a small incision and spreading it apart is less invasive than cutting a longer incision, provides less trauma to the tissue, and requires fewer stitches. However, it is problematic to properly spread the small incision, and at the same time insert a flexible graft material into the small opening and along the bone line to build up the gums. With existing conventional hand held instruments it is cumbersome for dentists implanting material for ridge augmentation to retract the soft tissue opening in a form suited to accommodate the shape and size of implant material for passage with one hand while maintaining separation of connective tissue and bone as implant material is being coaxed in with the other hand. Due to mental nerve inervation and shrinkage of soft tissue with re-absorption and narrowing of mandibular alveolar ridge the incision size is limited complicating an otherwise simple step in procedure. Often dentists will go through a pick-up-and-put-down routine of several different dental instruments to tend to the various acts of broaching, retracting, tissue separating, and implanting during a ridge augmentation, which is disruptive of the dentist's concentration and complicates what is otherwise a simple step in procedure. Moreover, often conventional instruments used to retract and maintain opening to the incision compromise or obstruct the available entrance space to the opening. Further complicating the process is the flexibility of existing graft material which does not remain rigid during the handling and insertion steps.

A need therefore remains for a dental surgical tool that will aid in the spreading of the incision and serve to guide the flexible graft material along under the gums and along the bone, to make the operation quicker and thus less traumatic to the individual. A need also remains for a method of using such a tool.

The following represents a list of known related art:

U.S. Pat. No. 6,083,225, to Winslow, et al., issued Jul. 4, 2000;

U.S. Pat. No. 5,891,147 to Moskovitz, et al., issued Apr. 6, 1999;

U.S. Pat. No. 5,961,329, to Stuck-McCormick, issued Oct. 5, 1999;

U.S. Pat. No. 5,915,962, to Rosenlicht, issued Jun. 29, 1999;

U.S. Pat. No. 5,759,033, to Elia, issued Jun. 2, 1998;

U.S. Pat. No. 5,397,235, to Elia, issued Mar. 14, 1995;

U.S. Pat. No. 4,024,639 to Weiss, et all, issued May 24, 1977; and

U.S. Pat. No. 4,872,840 to Bori, issued Oct. 10, 1989.

The teachings of each of the above-listed citations (which does not itself incorporate essential material by reference) are herein incorporated by reference. None of the above inventions and patents, taken either singularly or in combination, is seen to describe the instant invention as claimed. Thus solving the aforementioned problems is desired.

Heretofore, a surgical tunnel retractor as described herein has not previously been provided. A surgical tool designed for use in inserting bone graft material into the gum tissue of a patient and along the bone line to augment the bone line, which is minimally invasive, and which requires only a small incision, and which serves to guide the insertion of material into and under the tissue and along the target bone has not been provided. A surgical tool designed for use in inserting bone graft material into the gum tissue of a patient and along the alveolar ridge of the inferior or superior maxilla to augment the alveolar ridge, which is minimally invasive, and which requires only a small incision, and which serves to guide the insertion of augmentation material into and under the tissue and along the target alveolar ridge zone has not been provided.

Therefore, it is highly desirable to create an article and method to meet these needs and objects. Potential customers for articles and methods that meet these objects include dentists, dental and surgical supply companies, oral surgeons, hospitals, clinics, medics, etc.

DETAILED DESCRIPTION

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

Figure 1:
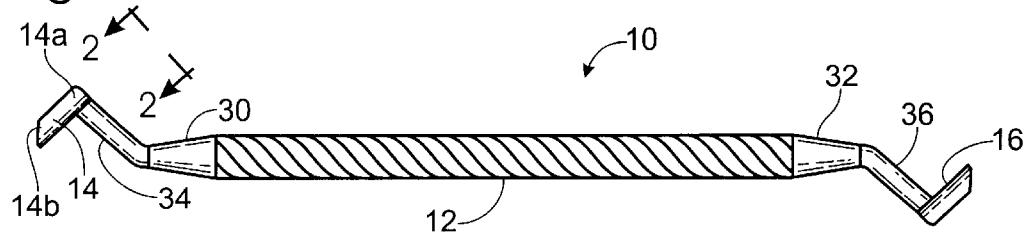
FIG. 1 shows an embodiment of the present invention.
Figure 3:
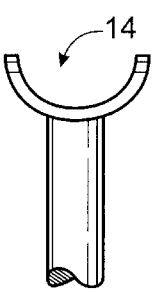
FIG. 3 shows a view of one of the half tube ends of the present invention.
Figure 4:
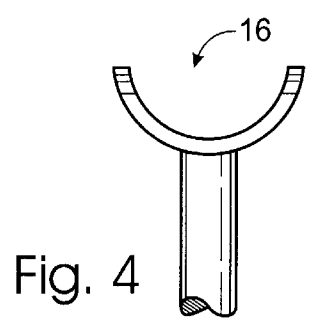
FIG. 4 shows a view of the other half tube end of the present invention.

A surgical tunnel retractor is provided. Referring to FIG. 1, a surgical tunnel retractor 10 according to the present invention is shown comprising an elongated handle 12 having opposing first and second ends, 30 and 32 respectively, and an arched plate member 14 connected to said first end 30 of said handle. As shown in FIG. 1, the surgical tunnel retractor can be further provided with a second arched plate member 16 connected to said second end 32 of said handle. As shown in FIGS. 3 and 4, the first and second arched plate members are preferably of different size to provide more options to the user, but the sizes need not be different. As shown in FIG. 1, said surgical tunnel retractor can be further provided with shank elements, 34 and 36, disposed between said handle ends and said arched plate members. The handle portion is preferably straight and tapered on both ends. Those skilled in the art will know that said handle be configured in numerous equivalent ways.

Figure 2:
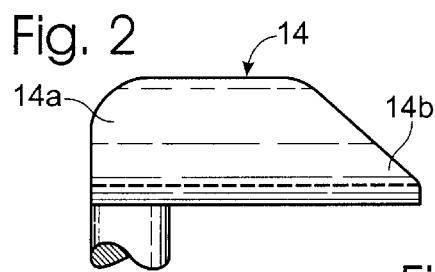
FIG. 2 shows a view of the embodiment displayed in FIG. 1 along the 2—2 line.
Figure 5:
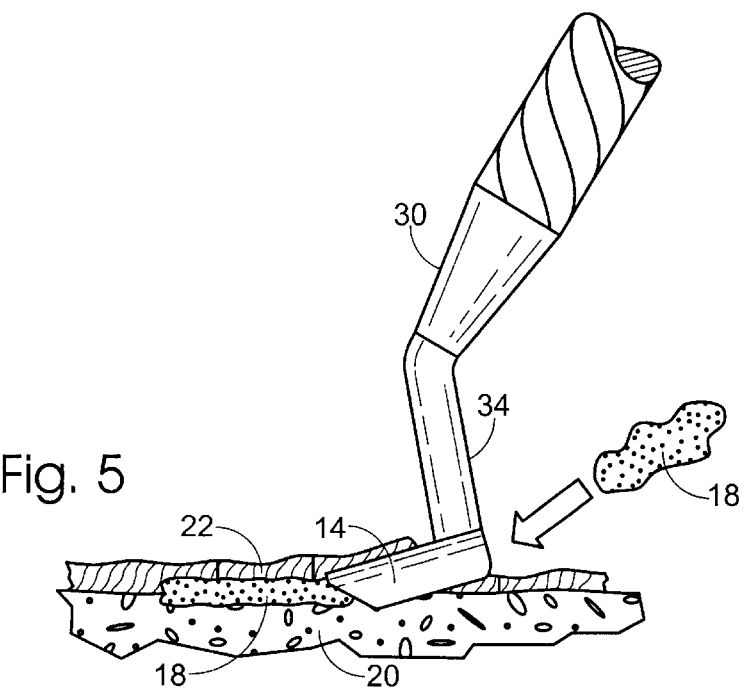
FIG. 5 shows an environmental view of an embodiment of the present invention in use.

The arched plate member is semi-circular in cross-sectional shape with proximal 14a and distal 14b ends in relation to handle, as shown in FIGS. 1, 2, 3, and 4. As shown in FIG. 2, towards the distal end 14b of said arched plate, the lateral edges of said plate taper into the curvature to the height of the arch, rounding off in plow-like tip for inserting in and under the gum tissue of patient. The tip, as seen in FIG. 5, provides for broaching incisions in soft tissue 22 while the arched plate member lifts and retracts the tissue in a convenient tunnel-like shape for passing materials 18 into, along, and under the tissue. The arch plate member can have a varying arc radius preferably in the range of 1.5 mm to 4 mm. The arch plate member preferably has a longitudinal length in the range of 4 mm to 20 mm. Those skilled in the art will know that said arched plate members be configured in numerous equivalent ways. The dimensions provided are adapted for use of the instrument on human patients. Those skilled in the art will know that the disclosed tunnel retractor can equally be used on non-human patients with a simplistic adaption of the foregoing dimensions to scale. The invention is thus not limited to human patients and by the foregoing dimensions.

When the surgical retractor is provided without shank elements, the arched plate members extend away from the handle at an obtuse angle to the longitudinal axis of the handle, with the distal ends of said plate members furthest away from the ends of said handle.

As shown in FIGS. 1, 2, 3, 4 and 5, when a shank element 34 is provided, the shank element connects to arched plate member at the proximal end 14a on the convex side of the arched plate at the general apex of said arched plate. The shank element connects to the arched plate member preferably to form right angle, 90 degrees, between the longitudinal axes of the arched plate member and the shank element, oppositely extending from the angle to which the shank element connects to the handle. The angle between the longitudinal axes of the shank element and the arched plate member can be any angle in the range of 10 degrees to 150 degrees. The shank element connects to the handle preferably to form an obtuse angle, preferably 135 degrees, between the longitudinal axes of the handle and the longitudinal axes of the shank. The obtuse angle between the longitudinal axes of the shank element and the handle can be any angle in the range of 60 degrees to 170 degrees.

The present invention is made of medical grade metal. Methods and procedures for making surgical implements of medical grade metal are well known in the art.

In operation, after a surgical incision is made into the gum tissue of a patient, cutting into the gingival membrane overlying the jawbone, the distal end of either the first or second arched plate members is inserted into the incision and along and under the gum tissue, with the arched plate member lifting and spreading the gum tissue, and the arched plate member creating a tunnel under the gum tissue and along the alveolar ridge of the jaw bone. This is displayed in FIG. 5. A portion of the arched plate member may remain outside of the gum tissue leaving an opening into the tunnel created by the insertion of the tunnel retractor portion. Material 18, which can be graft material, is pushed into the created tunnel, the arched plate member acting to guide the flexible graft material along under the gums and along the bone until the tunnel is filled. The graft material is tamped down. The arched plate member is then removed from incision and the tissue is closed over the cavity, and in some cases the tissue is sutured depending upon the size of the incision.

The present invention, while particularly well suited for use in the field of dentistry to aid in the provision of support for artificial teeth, is of general medical application for humans and other vertebrates. Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

I claim:

1. An surgical tunnel retractor, comprising:
   a. a handle having a first end and a second end; and
   b. a first arched plate member connected to said first end of said handle, said first plate member for broaching oral gum tissue and inserting said first plate member into tissue to form a tunnel-like opening into the tissue and along the alveolar ridge underlying the tissue.

2. The retractor of claim 1, further comprising:
   c. a second arched plate member connected to said second end of said handle, said second plate member for broaching oral gum tissue and inserting said second plate member into tissue to form a tunnel-like opening into the tissue and along the alveolar ridge underlying the tissue.

3. The retractor of claims 1 or 2, wherein a first shank element is disposed between said first end of said handle and said first plate member and a second shank element is disposed between said second end of said handle and said second plate member.

4. The retractor of claims 1 or 2, wherein said arch plate member has an arc radius in the range of 1.5 mm to 4 mm.

5. The retractor of claim 1 or 2, wherein said arch plate member has a longitudinal length in the range of 4 mm to 20 mm.

6. The retractor of claim 3, wherein a first shank element is disposed between said first end of said handle and said first plate member and a second shank element is disposed between said second end of said handle and said second plate member, wherein said arch plate member has an arc radius in the range of 1.5 mm to 4 mm, and wherein said arch plate member has a longitudinal length in the range of 4 mm to 20 mm.

7. A surgical tunnel retractor, comprising:
   a. a handle having a first end and a second end; and
   b. means provided on said first end for broaching oral gum tissue and forming a tunnel-like opening into the tissue and along the alveolar ridge underlying the tissue.

8. A hand-held instrument for use in broaching and dilating incisions in soft oral gum tissue, comprising:
   a. a handle having opposite first and second ends;
   b. an arched plate member connected to said handle, said member semi-circular in cross-sectional shape having first and second ends, said arched plate member having lateral edges tapered into arch curvature towards which the most forward position of said second end of said arched plate member rounds-off in plow-like shape; and
   c. a shank element disposed between said first end of said handle and said first end of said arched plate member.

9. A method of bone grafting, comprising:
   a. incising an oral gum tissue layer overlying the bone structure of the alveolar ridge to expose a portion of said structure;
   b. forming an elongate channel-shaped cavity in the tissue along the underlying the bone structure;
   c. inserting a retractor having an arched plate member into the incision to spread the tissue and to provide a tunnel guide for the graft material to be inserted along and under;
   d. inserting graft material along and under said arched plate member;
   e. pushing the graft material along and under the arched plate member, into the gum tissue and along the bone line until the graft material is inserted;
   f. removing the retractor; and
   g. then closing the tissue over said cavity.

* * * * *